United States Patent [19]

Rottloff et al.

[11] 4,028,393

[45] June 7, 1977

[54] PROCESS FOR THE PRODUCTION OF POLYFUNCTIONAL CYANIC ACID ESTERS

[75] Inventors: Günther Rottloff, Cologne; Rudolf Sundermann, Leverkusen; Ernst Grigat, Odenthal-Gloebusch; Rolf Putter, Duesseldorf, all of Germany

[73] Assignee: Bayer Aktiengesellschaft, Germany

[22] Filed: Feb. 17, 1976

[21] Appl. No.: 658,814

[30] Foreign Application Priority Data

Feb. 22, 1975 Germany .......................... 2507671
July 2, 1975 Germany .......................... 2529486

[52] U.S. Cl. .................... 260/453 P; 260/453 AR; 260/463
[51] Int. Cl.² ....................................... C07C 122/00
[58] Field of Search ...................... 260/453 P, 567.5

[56] References Cited

UNITED STATES PATENTS 3,553,244  1/1971  Grigat et al. .......................... 260/453
3,595,900  7/1971  Loudas et al. ......................... 260/453

Primary Examiner—Dolph H. Torrence
Attorney, Agent, or Firm—Connolly and Hutz

[57] ABSTRACT

Highly pure aromatic polyfunctional cyanic acid esters having a high stability in storage and being extraordinarily suitable for use as starting compound for the production of plastics by cyclopoly-tri-merization are obtained by a special process.

A di- or polytrialkyl ammonium phenolate of the formula:

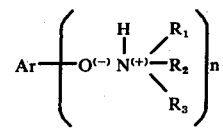

in which
Ar represents an optionally substituted aromatic radical,
$R_1$, $R_2$ and $R_3$ are the same or different and each represents a linear or branched alkyl radical, and
n is a number from 2 to 6, is reacted at a temperature in the range of from −40° to +65° C in the presence of a trialkyl amine and an organic solvent with an excess of cyanogen halide.

The excess of cyanogen halide is up to 80% by weight, based on the total weight of the phenolate and the trialkyl amine.

4 Claims, No Drawings

PROCESS FOR THE PRODUCTION OF POLYFUNCTIONAL CYANIC ACID ESTERS

This invention relates to a process for the production of highly pure, aromatic polyfunctional cyanic acid esters with high stability in storage.

It is known that monophenols or polyphenols optionally attached to a heterocyclic radical, carrying at most one sterically hindering substituent in the ortho position relative to each hydroxyl group can be reacted with halogen cyanides and a tertiary amine (molar ratio 1:1:1) in an inert organic medium at temperatures below 65° C (DT-PS No. 1,195,764).

It is also known that aromatic cyanic acid esters can be obtained by using an inorganic base which is capable of phenolate formation under the reaction conditions instead of a tertiary amine (DT-PS No. 1,248,668).

In addition, it is known from DT-PS No. 1,248,667 that phenols can be reacted with halogen cyanides and a base capable of phenolate formation under the reaction conditions at temperatures below 65° C in the presence of water and/or an alcohol or alcohol mixture as solvent.

In many cases, the polyfunctional cyanic acid esters obtained by this process do not have the requisite purity and stability in storage, so that they are not really suitable for use as starting compounds for the production of high molecular weight polytriazines (for example in accordance with DT-AS No. 1,190,184).

By contrast, it is already known that the reaction of phenolates with cyanogen halide gives trimeric products, mainly in the form of triazine derivatives. The trimeric products are formed by way of the imino carbonic acid phenyl esters which are also formed as a reaction product (Liebigs Ann. Chem. Vol 287, page 319 and Ber. detsch. Ges., Vol 28, page 2467).

It has now been found that highly pure polyfunctional aromatic cyanic acid esters can be obtained in high yields by reacting di- or poly-trialkyl ammonium phenolates with an excess of a halogen cyanide in the presence of a trialkyl amine in an organic solvent.

Suitable di- or poly-trialkyl ammonium phenolates are compounds corresponding to the general formula:

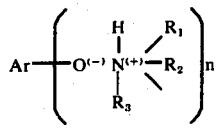

in which
Ar represents an optionally substituted aromatic radical and
$R_1$, $R_2$ and $R_3$ represent straight-chain and branched alkyl radicals preferably having from 1 to 9 carbon atoms more preferably from 1 to 5 carbon atoms, the radicals $R_1$, $R_2$, $R_3$ not having to be the same (for example methyl, ethyl, propyl, isopropyl, n-butyl, isobutyl, tert.butyl or the isomeric pentyl radicals, more especially methyl, ethyl or propyl),
$n$ is a number from 2 to 6, preferably from 2 to 4, and more especially the number 2.

Preferred optionally substituted aromatic radicals are radicals corresponding to the general formula:

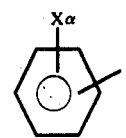

in which
X represents hydrogen, halogen, alkyl or phenyl; several radicals X do not have to be the same or two radicals X which substitute adjacent carbon atoms may even form with those carbon atoms a carbocyclic or heterocyclic 5-membered or 6-membered ring, and
$a$ stands for the number $6 - n$.

Another group of aryl radicals corresponds to the general formula:

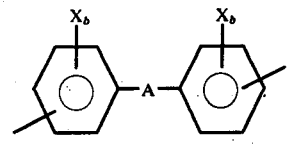

in which
A represents oxygen, the sulphonyl group ($-SO_2$), the carbonyl group ($-CO-$), sulphur ($-S-$), the carbonyl dioxy group

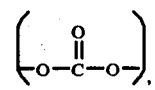

an alkylene chain having from 1 to 9 and preferably 1 to 6 carbon atoms, optionally substituted by lower alkyl radicals, preferably methyl, ethyl or phenyl, a cycloaliphatic or aromatic 5-membered or 6-membered ring, or a single bond, and
X preferably has the meaning defined above or represents the group

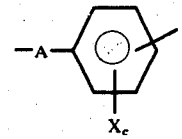

in which
A and X are as defined above and
$c$ stands for the number $5 - n$, and
$b$ stands for the number $5 - n$.

Of the halogens (fluorine, chlorine, bromine and iodine), fluorine, chlorine and bromine are preferred.

Suitable alkyl radicals are straight-chain and branched alkyl radicals having from 1 to 9 carbon atoms and preferably from 1 to 5 carbon atoms, for example methyl, ethyl, propyl, isopropyl, n-butyl, isobutyl, tert-butyl, and the isomeric pentyl radicals, more especially methyl, ethyl and tert-butyl.

The following are mentioned as examples of trialkyl ammonium phenolates: the bis-trimethyl ammonium salts, the bis-triethyl ammonium salts, the bis-dimethyl ethyl ammonium salts, the bis-methyl diethyl ammonium salts, the bis-dimethyl propyl ammonium salts, the bis-tripropyl ammonium salts and the bis-tributyl ammonium salts of the following bisphenols: m-, p-dihydroxy benzene, 2-tert-butyl hydroquinone, 2,4-dimethyl resorcinol, 2,5-di-tert-butyl hydroquinone, tetramethyl hydroquinone, 2,4,6-trimethyl resorcinol, 4-chlororesorcinol, dihydroxy naphthalenes such as, for example 1,4-, 1,5-, 1,6-, 1,7-, 2,6-, 2,7-dihydroxy naphthalene; dihydroxy diphenyls such as, for example, 4,4'-dihydroxy diphenyl, 2,2'-dihydroxy diphenyl, 3,3',5,5'-tetramethyl-4,4'-dihydroxy diphenyl,
3,3',5,5'-tetrachloro-4,4'-dihydroxy diphenyl,
3,3,40,5,5'-tetrachloro-2,2'-dihydroxy diphenyl,
2,2',6,6'-tetrachloro-4,4'-dihydroxy diphenyl,
4,4'-bis-[(3-hydroxy)-phenoxy]-diphenyl,
4,4'-bis-[(4-hydroxy)-phenoxy]-diphenyl,
2,2'-dihydroxy-1,1'-binaphthyl; dihydroxy diphenyl ethers, such as for example 4,4'-dihydroxy diphenyl ether,
3,3',5,5'-tetramethyl-4,4'-dihydroxy diphenyl ether,
3,3',5,5'-tetrachloro-4,4'-dihydroxy diphenyl ether,
4,4'-bis[p-hydroxyphenoxy]-diphenyl ether
4,4'-bis-[p-hydroxyphenylisopropyl]-diphenyl ether,
4,4'-bis-[p-hydroxy-phenoxy]-benzene,
4,4'-bis-[m-hydroxy-phenoxy]-diphenyl ether,
4,4'-bis-[4(4-hydroxyphenoxy)-phenylsulphone]-dipheny ether;

diphenyl sulphones, such as for example 4,4'-dihydroxy-diphenyl sulphone,
3,3',5,5'-tetramethyl-4,4'-dihydroxy-diphenyl sulphone,
3,3',5,5'-tetrachloro-4,4'-dihydroxy-diphenyl sulphone,
4,4'-bis-[p-hydroxyphenylisopropyl]-dipheny sulphone,
4,4'-bis [(4-hydroxy)-phenoxy]-diphenyl sulphone,
4,4'-bis-[(3-hydroxy)-phenoxy]-dipheny sulphone,
4,4'-bis-[4-(4-hydroxyphenyl-isopropyl)-phenoxy]-diphenyl sulphone
4,4'-bis [4-(4-hydroxyphenyl-sulphone)phenoxy]-diphenyl sulphone,
4,4'-bis-[4-(4-hydroxy)-diphenoxy]-diphenyl sulphone; dihydroxy dipheny alkanes, such as for example
4,4'-dihydroxy-diphenyl methane,
4,4'-bis-[p-hydroxy phenyl]-diphenyl methane,
2,2-bis-(p-hydroxyphenyl)-propane,
2,2-bis-(3,5-dimethyl-4-hydroxy-phenyl)propane,
2,2-bis(3,5-dichloro-4-hydroxy-phenyl)propane,
1,1-bis-[p-hydroxyphenyl]-cyclohexane,
bis-[2-hydroxy-1-naphthyl]-methane,
1,2-bis-[p-hydroxyphenyl]-1,1, 2,2-tetramethyl ethane;
4,4'-dihydroxy benzophenone,
4,4'-bis-(4-hydroxy)phenoxy-benzophenone,
1,4-bis-[p-hydroxy phenyl isopropyl]-benzene,
phloroglucinol, 2,2'-, 5'5'-tetrahydroxy-diphenyl sulphone.

Cyanogen chloride and cyanogen bromide, both of which are readily obtainable, may be used as the cyanogen halides.

The trialkyl amines used are compounds preferably corresponding to the general formula:

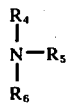

in which
R$_4$, R$_5$ and R$_6$ are the same or different and represent alkyl groups having from 1 to 36 carbon atoms, more especially from 1 to 18 carbon atoms, phenyl and/or cycloalkyl having from 4 to 7 carbon atoms, more especially from 5 to 6 carbon atoms, or cycloalkyl radicals having 6 carbon atoms interrupted by C$_1$ to C$_4$ alkylene groups.

The following are mentioned as examples of trialkyl amines of this kind: trimethyl amine, triethyl amine, methyl diethyl amine, tripropyl amine, tributyl amine, methyl dibutyl amine, dinonyl methyl amine, dimethyl stearyl amine, dimethyl cyclohexyl amine and diethyl aniline.

The trialkyl amine used in the process according to the invention is preferably employed in quantities of from 0.1 to 20% by weight and more especially in quantities of from 1 to 5% by weight, based on the di- or poly-trialkyl ammonium phenolate.

The quantity in which the cyanogen halide is added is always greater than the sum of the di- or poly-trialkyl ammonium phenolate used and the trialkyl amine used. The excess may amount to 80% by weight, and more especially to 40% by weight, based on the sums of the quantities by weight of the above components.

The following solvents, for example, may be used in the process according to the invention: lower aliphatic alcohols, such as methanol, ethanol, propanol or isopropanol; aliphatic ketones such as acetone, methyl ethyl ketone, diethyl ketone, methyl isopropyl ketone or methyl isobutyl ketone; aliphatic or aromatic hydrocarbons, preferred aliphatic hydrocarbons being the fractions accumulating during the distillation of naturally occurring mixtures, such as petroleum ether, light petrol or petrol, whilst preferred aromatic hydrocarbons are, for example, benzene, toluene and the xylenes; aliphatic and aromatic chlorinated hydrocarbons such as dichloromethane, dichloroethane, perchlorethylene, chlorobenzene or dichlorobenzene; ethers such as diethyl ether, diisopropyl ether or di-sec-butyl ether; nitro hydrocarbons such as nitromethane, nitrobenzene or nitrotoluene, and mixtures thereof.

The process according to the invention is generally carried out at temperatures in the range of from −40° C to +65° C and preferably at temperatures in the range of from 0° C to 30° C. In cases where cyanogen chloride is used, the reaction is preferably carried out below the boiling point (13° C), although in cases where cyanogen bromide is used it is even possible to apply temperatures of above 50° C.

In general, the process according to the invention is carried out by introducing the bis- or poly- trialkyl ammonium phenolate and the trialkyl amine, in solution in the solvent, to a thoroughly stirred solution of cyanogen halide in the solvent. The polyfunctional cyanic acid esters precipitate with the trialkyl ammonium halide and may be isolated by known methods, such as filtration, vacuum filtration or centrifuging.

Minor impurities such as unreacted starting material or aromatic hydroxyl compounds reacted on one OH-group only, but also imino carbonic acid esters, reduce stability in storage to a very considerable extent, especially at elevated temperatures (20° to 50° C). Thus, it is not possible according to the prior art to obtain resorcinol dicyanate for example with a stability in storage at room temperature of only a few weeks. This pooor stability in storage also has an adverse effect upon processibility into polytriazines (for example in accordance with DT-AS No. 1,190,184). Since the impurities act as polymerisation catalysts, it is frequently not possible to process the polyfunctional cyanic acid esters obtained in accordance with the prior art under controlled conditions. In many cases, polymerisation takes place much too quickly and exothermically so that the heat of reaction cannot always be uniformly dissipated. This occasionally results in complete destruction of the polymers.

It is extremely surprising that the aromatic polyfunctional cyanic acid esters are obtained in highly pure form by the process according to the invention, so that adequate stability in storage can be obtained and controllable processing into polytriazines is now possible.

The aromatic polyfunctinal cyanic acid esters are valuable starting materials for the production of plastics. They can be polymerised by known processes (for example in accordance with DT-AS No. 1,190,184) to form high molecular weight polytriazines which may be used in various fields, for example as fibre-reinforced plastics, moulding and casting resins, adhesives, coating agents or lacquers.

The invention is illustrated by, but by no means limited to, the following Examples in which the percentages quoted are percentages by weight.

EXAMPLE 1

In a 3 liter glass vessel, equipped with a thermometer and an inlet pipe projecting below the surface of the liquid, 1 liter of isopropanol is cooled to between 0° C and −5° C, followed by the addition of 271 g (4.4 mols) of cyanogen chloride. A precooled solution of 456 g (2 mols) of 2,2-bis-(p-hydroxyphenyl)-propane and 420 g (4.04 mols) of triethyl amine in 1liter of isopropanol is pumped in with stirring below the surface over a period of 40 to 60 minutes by means of a metering pump. The reaction temperature is best kept at −5° C to +3° C. On completion of the reaction, the cystalline sludge formed is allowed to cool and is filtered off under suction from the isopropanol. The filter residue is thoroughly stirred with 600 ml of water and then filtered off under suction. The filter residue thus obtained is washed thoroughly with water and a completely crystalline dicyanate is obtained after drying in a stream of air at 35° to 40° C. Yield: 525 g (95% of the theoretical), mp: 82° C, $n_D^{90}$ : 1.5380.

The dicyanate obtained poly-tri-merized within 36 hours at 150° C up to a conversion of 48% of the cyanate groups and is extraordinarily suitable as starting compound for the production of plastics in accordance with DT-AS No. 1,190,184. Contrary thereto, the same dicyanate obtained according to the process of DT-PS No. 1,195,764 or DT-PS No. 1,248,668 poly-tri-merizes strongly exothermic and uncontrollable up to conversion of 48% within 1 to 5 hours at 150° C.

EXAMPLE 2

In a 3 liter glass vessel, equipped with a thermometer and in inlet pipe projecting below the surface of the liquid, a solution of 271 g (4.4 mols) of cyanogen chloride in 1 liter of isopropanol is cooled to −5° C. A precooled solution of 456 g (2 mols) of 2,2-bis-(p-hydroxyphenyl)-propane and 420 g (4.04 mols) of triethyl amine in 1 liter of isopropanol is pumped in below the surface while stirring over a period of 40 to 60 minutes by means of a metering pump. The reaction temperature is best kept at −5° C to +3° C. On completion of the reaction, the crystalline sludge formed is allowed to cool and filtered off under suction from the isopropanol. The filter residue is washed with 100 ml of isopropanol and is then thoroughly stirred with 600 ml of water and filtered off under suction. The filter residue thus obtained is dissolved in 1.5 liter of toluene and washed with water until free from chloride. The solvent is then distilled off. Solvent residues are removed at a temperature of 95° C and under a pressure of 10 Torr. 514 g (93% of the theoretical) of diandicyanate are obtained after cooling. Mp: 82° C, $n_D^{90}$ : 1.5380

The time of polytri-merization up to a conversion of 48% of the cyanate-groups is 48 hours at 150° C.

EXAMPLE 3

A solution of 271 g (4.4 mols) of cyanogen chloride in 1.1 liter of isopropanol is introduced at 0° to −5° C into a 3 liter glass vessel equipped with a stirrer and a thermometer. By means of a metering pump, a solution of 220 g (2 mols) of resorcinol and 420 g (4.04 mols) of triethyl amine in 750 ml of isopropanol is introduced with stirring through an inlet pipe projecting below the surface. The pumping rate is adjusted in such a way that the reaction temperature can be kept at −5° C to +3° C. On completion of the reaction, the crystalline sludge formed is filtered off under suction from the isopropanol. The filter residue is thoroughly stirred with 1.1 liter of water and filtered off under suction again. The residue thus obtained is then thoroughly washed with water and dried in a stream of air at 25° to 30° C. 276 g (86% of the theoretical) of resorcinol dicyanate are obtained in this way. Mp: 81° C, $n_D^{80}$ : 1.4980

The polymerization-time up to conversion of 40 to 45% of the cyanato groups is 14 hours at 150° C whilst resorcinol dicyanate obtained according to DT-PS No. 1,195,764 or DT-PS No. 1,248,668 polymerizes in a strongly exothermic reaction under decomposition at a temperature above 120° C.

EXAMPLE 4

271 g (4.4 mols) of cyanogen chloride in 1.1 liter of isopropanol are introduced at −5° C into a 3 liter glass vessel equipped with a stirrer, a thermometer and an inlet pipe. By means of a metering pump, a solution of 220 g (2 mols) of resorcinol and 430 g (4.04 mols) of triethyl amine in 750 ml of isopropanol is pumped in below the surface with stirring. The reaction temperature is best kept at −5° C to +3° C. On completion of the reaction, the crystalline sludge formed is filtered off under suction from the isopropanol and the filter residue is washed with 100 ml of isopropanol. The residue is thoroughly stirred with 1.1 liter of water and filtered off under suction again. The filter residue is then taken up in 800 ml of methylene chloride and washed with water until free from chloride. Following the addition of 600 ml of perchloroethylene, the methylene chloride distils off initially at 45° to 50° C and subsequently at 60° C and at about 160 Torr. The residue is left to cool with stirring to 5°–10° C and the resorcinol dicyanate which has crystallised out is filtered off under suction, washed twice with 50 ml of perchloroethylene and dried in a stream of air. 270 g (84% of the theoretical)

of resorcinol cyanate are obtained. Mp: 81° C, $n_D^{90}$: 1.4980

The polymerization time of the dicyanate obtained up to conversion of 45% is 18 hours at 150° C.

EXAMPLE 5

Following the procedure of Example 1, a solution consisting of 0.8 l of isopropanol and 135 g (2.2 mols) of cyanogen chloride is reacted at −5° to +3° C with a solution consisting of 308 g (1 mol) of dihydroxy spiroindane:

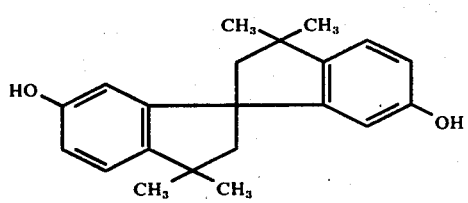

210 g (2.02 mols) of triethyl amine and 1 liter of isopropanol. On completion of the reaction, the crystalline sludge formed is filtered off under suction. The filter residue is washed first with 100 ml of isopropanol and then thoroughly with water. After drying in a stream of air at approximately 35° C, a crystalline dicyanate melting at 123° to 124° C is obtained in a yield of 330 g (92% of the theoretical).

EXAMPLE 6

A solution consistig of 284 g (1 mol) of 2,2-bis-(3,5-dimethyl-4-hydroxyphenyl)-propane, 210 g (2.02 mols) of triethyl amine and 0.8 liter of isopropanol, is added dropwise at −5° to +3° C to a solution of 0.8 liter of isopropanol and 129 g (2.1 mols) of cyanogen chloride. Working up is carried out in the same way as described in Example 5, giving 314 g (94% of the theoretical) of a dicyanate melting at 135° to 136° C.

EXAMPLE 7

A solution of 135 g (2.2 mols) of cyanogen chloride in 0.5 liter of isopropanol, precooled to −5° C, is reacted as described in Example 1 with a solution of 186 g (1 mol) of 4,4'-dihydroxy diphenyl and 210 g (2.02 mols) of triethyl amine in 1.6 liters of isopropanol. The crystalline sludge formed is filtered off under suction when cold and washed twice with 2 × 100 ml portions of a 1:1 water:isopropanol mixture. After thorough washing with water and drying in a stream of air at a maximum temperature of 35° C, a dicyanate melting at 137° to 138° C is obtained in a yield of 212 g (90% of the theoretical).

EXAMPLE 8

1 liter of isopropanol is mixed at −5° C with 129 g (2.1 mols) of cyanogen chloride and the resulting mixture is reacted as described in Example 1 with a solution of 268 g (1 mol) of 1,1-bis-(4-hydroxyphenyl)-cyclohexane and 210 g (2.02 mols) of triethyl amine in 0.5 liter of acetone. The crystalline sludge formed is filtered off under suction when cold and worked up in the same way as described in Example 7. After drying in a stream of air at a maximum temperature of 25° C, a dicyanate melting at 58.5 to 59.5° C is obtained in a yield of 280 g (88% of the theoretical).

EXAMPLE 9

A mixture of 67.6 g (1.1 mol) of cyanogen chloride and 0.5 liter of di-sec-butyl ether, precooled to −5° C, is reacted with a solution consisting of 66 g (0.5 mol) of resorcinol, 106 g (1.05 mol) of triethyl amine and 30 ml of dimethyl formamide at a temperature of −5° C. The crystalline sludge formed is filtered off under suction when cold and washed in portions with 100 ml of di-sec-butyl ether. The filter residue, freed from the solvent in a stream of air, is suspended in plenty of water, filtered under suction and washed thoroughly with water. After drying, a dicyanate melting at 79° to 81° C is obtained in a yield of 65.6 g (82% of the theoretical).

EXAMPLE 10

A solution consisting of 114 g (0.5 mol) of 2,2-bis-(4-hydroxyphenyl)-propane, 106 g (1.05 mol) of triethyl amine and 0.6 liter of toluene, is added dropwise at −5° C to +3° C to a solution of 67.6 g (1.1 mol) of cyanogen chloride in 0.6 liter of ligroin. On completion of the reaction, the crystalline sludge formed is filtered sharply under suction. The filter residue is washed in portions with a little cold toluene and freed from the solvent in a stream of air at room temperature. The product is then suspended in plenty of water, filtered under suction and thoroughly washed. A dicyanate melting at 80° to 81° C is left behind in a yield of 125 g (90% of the theoretcal).

EXAMPLE 11

In a 3 liter glass vessel, equipped with a thermometer and an inlet pipe projecting below the surface of the liquid, 1 liter of isopropanol is cooled to between 0° C and −5° C followed by the addition of 271 g (4.4 mols) of cyanogen chloride. By means of a metering pump, a precooled solution of 456 g (2 mols) of 2,2-bis-(p-hydroxyphenyl)-propane, 413 g (4 mols) of 98% triethyl amine and 16.1 g (0.1 mol) of decyl dimethyl amine in 1 liter of isopropanol is pumped in below the surface with stirring over a period of 40 to 60 minutes. The reaction temperature is best kept at −5° C to +3° C. On completion of the reaction, the crystalline sludge formed is allowed to cool and filtered under suction from the isopropanol. The filter residue is stirred thoroughly with 600 ml of water and filtered under suction. The filter residue thus obtained is thoroughly washed with water, and a completely crystalline dicyanate is obtained after drying in a stream of air at 35° to 40° C. Yield: 525 g (95% of the theoretical), mp: 82° C, $n_D^{90}$: 1.5380.

EXAMPLE 12

In a 3 liter glass vessel, equipped with a thermometer and in inlet pipe projecting below the surface of the liquid, a solution of 271 g (4.4 mols) of cyanogen chloride in 1 liter of isopropanol is cooled to −5° C. By means of a metering pump, a precooled solution of 456 g (2 mols) of 2,2-bis-(p-hydroxyphenyl)propane and 285 g (4.04 mols) of trimethyl amine in 1 liter of isopropanol, is pumped in below the surface with stirring over a period of 40 to 60 minutes. The reaction temperature is best kept at −5° to +3° C. On completion of the reaction, the crystalline sludge formed is allowed to cool and filtered under suction from the isopropanol. The filter residue is washed with 100 ml of isopropanol and then thoroughly stirred with 600 ml of water and filtered under suction. The filter residue obtained is dissolved in 1.5 liter of toluene and washed with water until free from chloride. The solvent is then distilled off. Solvent residues are removed at a temperature of 95° C and under a pressure of 10 Torr. After cooling, a diandicyanate is obtained in a yield of 514 g (93% of the theoretical). Mp: 82° C, $n_D^{90}$ :1.5380.

We claim:

1. A process for the production of a polyfunctional aromatic cyanic acid ester which comprises reacting an excess of a cyanogen halide, in the presence of a trialkyl amine and an organic solvent with a di- or poly-trialkyl ammonium phenolate of the formula:

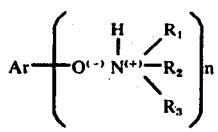

in which

Ar represents an optionally substituted aromatic radical, $R_1$, $R_2$ and $R_3$ are the same or different and each represents a linear or branched alkyl radical, and $n$ is a number from 2 to 6.

2. A process as claimed in claim 1, wherein the excess of cyanogen halide is up to 80% by weight, based on the total weight of the phenolate and the trialkyl amine.

3. A process as claimed in claim 1, wherein the trialkyl amine is used in a quantity of from 0.1 to 20% by weight, based on the phenolate.

4. A process as claimed in claim 1 wherein the reaction is carried out at a temperature in the range of from −40° to +65° C.

* * * * *